(12) United States Patent
Sawhney et al.

(10) Patent No.: US 7,862,538 B2
(45) Date of Patent: Jan. 4, 2011

(54) SURGICAL DELIVERY SYSTEM FOR MEDICAL SEALANT

(75) Inventors: Amarpreet S. Sawhney, Lexington, MA (US); William H. Ransone, II, Waltham, MA (US); Mukesh Singhal, Allston, MA (US)

(73) Assignee: Incept LLC, Bedford, MA (US)

( * ) Notice: Subject to any disclaimer, the term of this patent is extended or adjusted under 35 U.S.C. 154(b) by 47 days.

(21) Appl. No.: 12/012,606

(22) Filed: Feb. 4, 2008

(65) Prior Publication Data

US 2009/0198177 A1    Aug. 6, 2009

(51) Int. Cl.
*A61M 37/00*    (2006.01)
(52) U.S. Cl. ........................................ 604/82
(58) Field of Classification Search ............ 604/82
See application file for complete search history.

(56) References Cited

U.S. PATENT DOCUMENTS

| | | | |
|---|---|---|---|
| 703,101 A | | 6/1902 | Ware |
| 3,158,183 A | | 11/1964 | Brown et al. |
| 4,117,728 A | | 10/1978 | Johnson |
| 4,341,218 A | | 7/1982 | Ü |
| 4,641,653 A | | 2/1987 | Rockey |
| 4,728,328 A | | 3/1988 | Hughes et al. |
| 5,100,992 A | | 3/1992 | Cohn et al. |
| 5,154,702 A | | 10/1992 | Foyil |
| 5,272,012 A | | 12/1993 | Opolski |
| 5,286,257 A | * | 2/1994 | Fischer ........................ 604/82 |
| 5,368,563 A | | 11/1994 | Lonneman et al. |
| 5,410,016 A | | 4/1995 | Hubbell et al. |
| 5,425,580 A | * | 6/1995 | Beller ......................... 366/131 |
| 5,464,396 A | | 11/1995 | Barta et al. |
| 5,466,680 A | * | 11/1995 | Rudy .......................... 514/57 |
| 5,514,379 A | | 5/1996 | Weissleder et al. |
| 5,530,528 A | | 6/1996 | Houki et al. |
| 5,534,024 A | | 7/1996 | Rogers et al. |
| 5,603,991 A | | 2/1997 | Kupiecki et al. |
| 5,665,117 A | | 9/1997 | Rhodes |
| 5,690,671 A | | 11/1997 | McGurk et al. |

(Continued)

FOREIGN PATENT DOCUMENTS

WO    9812274 A1    3/1998

(Continued)

OTHER PUBLICATIONS

IFU for Improved OcuSeal Pen Applicator Lots HBMT-0010-180 and HBMT-0010-180A.

(Continued)

*Primary Examiner*—Nicholas D Lucchesi
*Assistant Examiner*—Diva Ranade
(74) *Attorney, Agent, or Firm*—Dardi & Herbert, PLLC

(57) ABSTRACT

Described herein are systems for packaging dual or multiple-component adhesive systems that provide enhanced convenience and efficacy. In one aspect, the components of such a system may be divided into containers that allow for foolproof mixing schemes to avoid mixing the wrong components while also providing a sterile surface for mixing materials, with the sterile surface having optimal physical properties for mixing the materials, especially in small amounts. Certain embodiments include a surgical delivery system for a medical sealant including a packaging system with a detachable a sterile surface for mixing the sealant as needed for application.

23 Claims, 4 Drawing Sheets

U.S. PATENT DOCUMENTS

| | | | |
|---|---|---|---|
| 5,693,088 | A | 12/1997 | Lazarus |
| 5,714,159 | A | 2/1998 | Shalaby |
| 5,752,974 | A | 5/1998 | Rhee et al. |
| 5,769,882 | A | 6/1998 | Fogarty et al. |
| 5,823,198 | A | 10/1998 | Jones et al. |
| 5,824,037 | A | 10/1998 | Fogarty et al. |
| 5,843,160 | A | 12/1998 | Rhodes |
| 5,851,508 | A | 12/1998 | Greff et al. |
| 5,874,500 | A | 2/1999 | Rhee et al. |
| 5,876,448 | A | 3/1999 | Thompson et al. |
| 5,932,462 | A | 8/1999 | Harris et al. |
| 5,962,023 | A | 10/1999 | Jamiolkowski et al. |
| 5,994,750 | A | 11/1999 | Yagi et al. |
| 6,066,564 | A | 5/2000 | Li et al. |
| 6,110,198 | A | 8/2000 | Fogarty et al. |
| 6,149,614 | A | 11/2000 | Dunshee et al. |
| 6,168,592 | B1 | 1/2001 | Kupiecki et al. |
| 6,190,402 | B1 | 2/2001 | Horton et al. |
| 6,193,745 | B1 | 2/2001 | Fogarty et al. |
| 6,196,230 | B1 | 3/2001 | Hall et al. |
| 6,220,246 | B1 | 4/2001 | Chandler et al. |
| 6,261,305 | B1 | 7/2001 | Marotta et al. |
| 6,283,991 | B1 | 9/2001 | Cox et al. |
| 6,296,603 | B1 | 10/2001 | Turnlund et al. |
| 6,299,597 | B1 | 10/2001 | Buscemi et al. |
| 6,312,462 | B1 | 11/2001 | McDermott et al. |
| 6,312,463 | B1 | 11/2001 | Rourke et al. |
| 1,184,131 | A1 | 12/2001 | Abrams |
| 6,334,869 | B1 | 1/2002 | Leonhardt et al. |
| 6,371,975 | B2 | 4/2002 | Cruise et al. |
| 6,379,373 | B1 | 4/2002 | Sawhney et al. |
| 6,409,757 | B1 | 6/2002 | Trout, III et al. |
| 6,458,147 | B1 | 10/2002 | Cruise et al. |
| 6,463,317 | B1 | 10/2002 | Kucharczyk et al. |
| 6,506,204 | B2 | 1/2003 | Mazzocchi |
| 6,514,534 | B1 | 2/2003 | Sawhney |
| 6,544,276 | B1 | 4/2003 | Azizi |
| 6,566,406 | B1 | 5/2003 | Pathak et al. |
| 6,592,614 | B2 | 7/2003 | Lenker et al. |
| 6,605,294 | B2 | 8/2003 | Sawhney |
| 6,610,033 | B1 | 8/2003 | Melanson et al. |
| 6,613,037 | B2 | 9/2003 | Khosravi et al. |
| 6,632,457 | B1 | 10/2003 | Sawhney |
| 6,656,214 | B1 | 12/2003 | Fogarty et al. |
| 6,663,607 | B2 | 12/2003 | Slaikeu et al. |
| 6,663,667 | B2 | 12/2003 | Dehdashtian et al. |
| 6,673,093 | B1 | 1/2004 | Sawhney |
| 6,703,047 | B2 | 3/2004 | Sawhney et al. |
| 6,711,879 | B2 | 3/2004 | Korteweg et al. |
| 6,730,119 | B1 | 5/2004 | Smalling |
| 6,818,018 | B1 | 11/2004 | Sawhney |
| 6,827,735 | B2 | 12/2004 | Greenberg |
| 6,843,803 | B2 | 1/2005 | Ryan et al. |
| 6,918,926 | B2 | 7/2005 | Letort |
| 6,960,227 | B2 | 11/2005 | Jones et al. |
| 7,077,827 | B2 * | 7/2006 | Greenfield ............... 604/191 |
| 7,211,651 | B2 | 5/2007 | Pathak |
| 7,290,573 | B2 * | 11/2007 | Py et al. .................. 141/329 |
| 2001/0037091 | A1 * | 11/2001 | Wironen et al. ........... 604/236 |
| 2002/0026217 | A1 | 2/2002 | Baker et al. |
| 2002/0045848 | A1 | 4/2002 | Jaafar et al. |
| 2002/0049405 | A1 * | 4/2002 | Deslauriers et al. ........... 604/82 |
| 2002/0052643 | A1 | 5/2002 | Wholey et al. |
| 2002/0055708 | A1 * | 5/2002 | Peterson .................... 604/82 |
| 2002/0072703 | A1 * | 6/2002 | Nollert et al. ............... 604/82 |
| 2002/0101785 | A1 * | 8/2002 | Edwards et al. ............ 366/268 |
| 2003/0014075 | A1 | 1/2003 | Rosenbluth et al. |
| 2003/0051735 | A1 | 3/2003 | Pavcnik et al. |
| 2003/0077242 | A1 * | 4/2003 | Sawhney ................. 424/78.26 |
| 2003/0130725 | A1 | 7/2003 | DePalma et al. |
| 2003/0135269 | A1 | 7/2003 | Swanstrom |
| 2003/0204242 | A1 | 10/2003 | Zarins et al. |
| 2003/0204249 | A1 | 10/2003 | Letort |
| 2003/0216802 | A1 | 11/2003 | Chobotov |
| 2004/0016997 | A1 | 1/2004 | Ushio |
| 2004/0044358 | A1 | 3/2004 | Khosravi et al. |
| 2004/0082989 | A1 | 4/2004 | Cook et al. |
| 2004/0098096 | A1 | 5/2004 | Eton |
| 2004/0127846 | A1 * | 7/2004 | Dunn et al. ................ 604/82 |
| 2004/0204755 | A1 | 10/2004 | Robin |
| 2005/0004660 | A1 | 1/2005 | Rosenbluth et al. |
| 2005/0028484 | A1 | 2/2005 | Littlewood |
| 2005/0065592 | A1 | 3/2005 | Holzer |
| 2005/0209555 | A1 | 9/2005 | Middleton et al. |
| 2006/0025853 | A1 | 2/2006 | Evans et al. |
| 2006/0177481 | A1 * | 8/2006 | Sawhney .................. 424/426 |
| 2006/0275336 | A1 * | 12/2006 | Du Plessis ................. 424/423 |
| 2007/0255200 | A1 * | 11/2007 | McLean et al. .............. 604/82 |
| 2007/0255201 | A1 * | 11/2007 | McLean et al. .............. 604/82 |
| 2008/0275387 | A1 * | 11/2008 | Yeadon et al. ............... 604/82 |
| 2009/0017097 | A1 | 1/2009 | Sawhney et al. |

FOREIGN PATENT DOCUMENTS

| | | | |
|---|---|---|---|
| WO | 9835631 | A1 | 8/1998 |
| WO | 0009199 | A1 | 8/1999 |
| WO | 0051522 | A1 | 8/2000 |
| WO | 0121108 | A1 | 3/2001 |
| WO | 0166038 | A2 | 9/2001 |
| WO | 02102282 | A1 | 12/2002 |
| WO | 2006031358 | A2 | 3/2006 |
| WO | 2006031388 | A2 | 3/2006 |
| WO | 2007001926 | A2 | 1/2007 |

OTHER PUBLICATIONS

Confluent Surgical Duraseal packaging, Ref. 10-5005, LCN-2005-101, Rev. 02.

CoSeal Surgical Sealant, 0700169 Rev. 2. Date Mar. 2006.

* cited by examiner

SURGICAL DELIVERY SYSTEM FOR MEDICAL SEALANT

TECHNICAL FIELD

The technical field is related to a surgical delivery system for a medical sealant, and covers a packaging system with a detachable sterile surface for mixing the sealant as needed for application.

BACKGROUND

Dual syringe or sprayer systems for delivering dual component materials are known, e.g., as in U.S. Pat. Nos. 5,368,563, 5,464,396, 6,610,033, and 6,066,564, each of which are hereby incorporated by reference herein to the extent they do not contradict what is explicitly disclosed herein.

SUMMARY OF THE INVENTION

Mixing and applying dual component sealants in a medical procedure is challenging because using a sealant is only one step in a complex process that often requires managing a patient's safety and comfort to accomplish a delicate procedure, all the while maintaining sterile conditions. Dual component sealant systems often offer advantages for long term storage and control of sealant properties but nonetheless require mixing two (or more) components in the midst of these other considerations.

Described herein, however, are systems for packaging dual or multiple-component adhesive systems that provide enhanced convenience and efficacy. In one aspect, the components of such a system may be divided into containers that allow for foolproof mixing schemes to avoid mixing the wrong components while also providing a sterile surface for mixing materials, with the and sterile surface having optimal physical properties for mixing the materials repetitively, especially in small amounts. In fact, conventional dual syringe or sprayer systems are typically difficult or impossible to use when applying small amounts, especially if small amounts of sealant are to be replied repetitively.

In some embodiments, moreover, a sealant is provided that gels quickly on the site of intended use to provide an advantage of minimizing unwanted delay and providing gelation before the sealant flows away from the intended site of therapy.

Accordingly, in one embodiment, a single housing may be used that has a set of syringes with sealant components that can be mixed only with each other before the sealant is immediately required. A separate accelerator is provided for mixing with the other components when the user is ready to apply the sealant, with the working time after mixing with the sealant being short. The housing includes a small sterile surface that the user may remove and place as most appropriate for mixing. The sterile surface may advantageously be part of component packaging inside the housing so that a user may simultaneously open a sterile package to remove a component and also liberate the sterile surface for use.

DETAILED DESCRIPTION OF PREFERRED EMBODIMENTS

Figure 1:
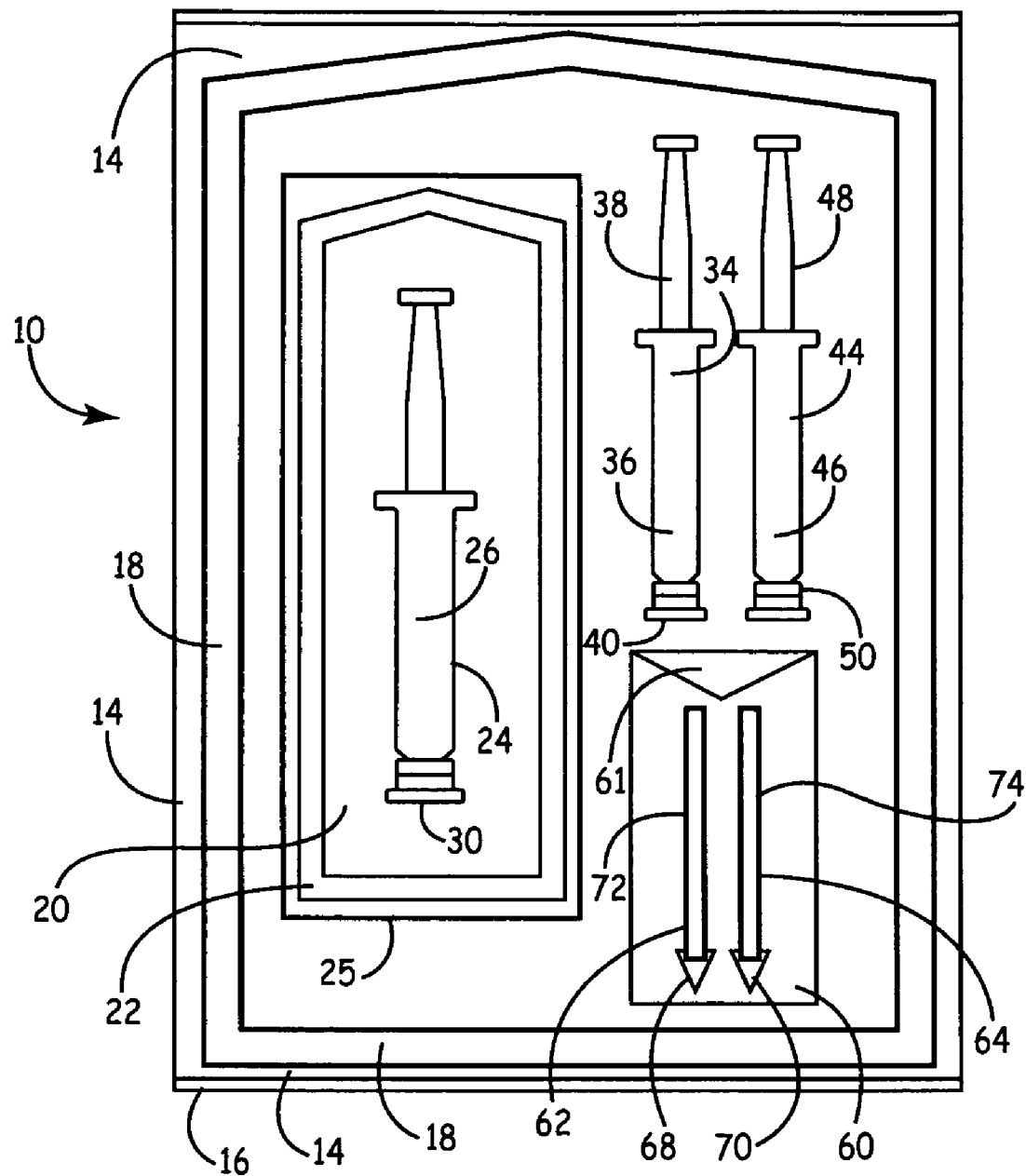
FIG. 1 is a schematic of a system for mixing small volumes of sealants.

FIG. 1 is a schematic of system 10 with a unitary housing provided as pouch 12 that has translucent upper covering 14 joined to bottom 16 along impermeable border 18 that seals the upper covering 14 to the bottom 16. As a schematic, it demonstrates an embodiment of the invention schematically, e.g., with some of the pouches being depicted with their contents visible. Inner removable pouch 20 has covering 22 joined to impermeable sterile surface 25 that serves as a backing. Inside pouch 20 is syringe 24 with barrel 26, plunger 28, and cap 30. Diluent syringe 34 has barrel 36, plunger 38, and cap 40. Accelerator syringe 44 has barrel 46, plunger 48, and cap 50. Inner removable applicator pouch 60 has flap 61 and contains applicators 62, 64, with soft sponge tips 68, 70, and stir rod ends 72, 74.

Figure 2:
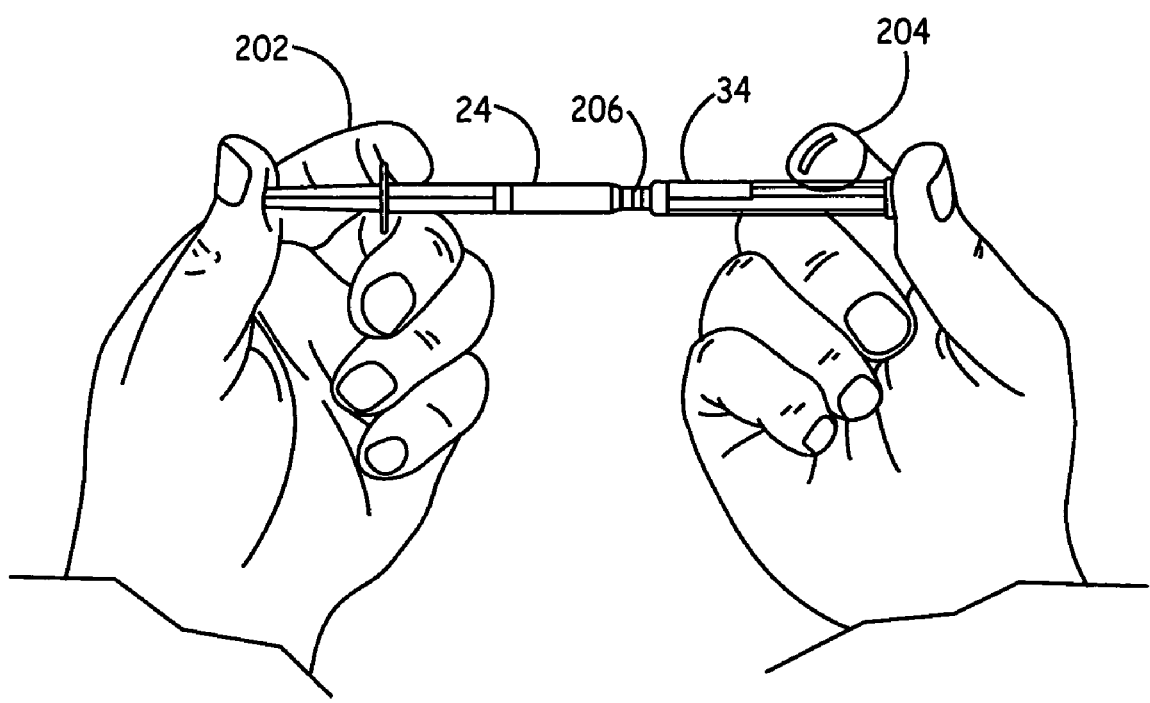
FIG. 2 depicts syringe-to-syringe mixing using components of the embodiment of FIG. 1.
Figure 3:
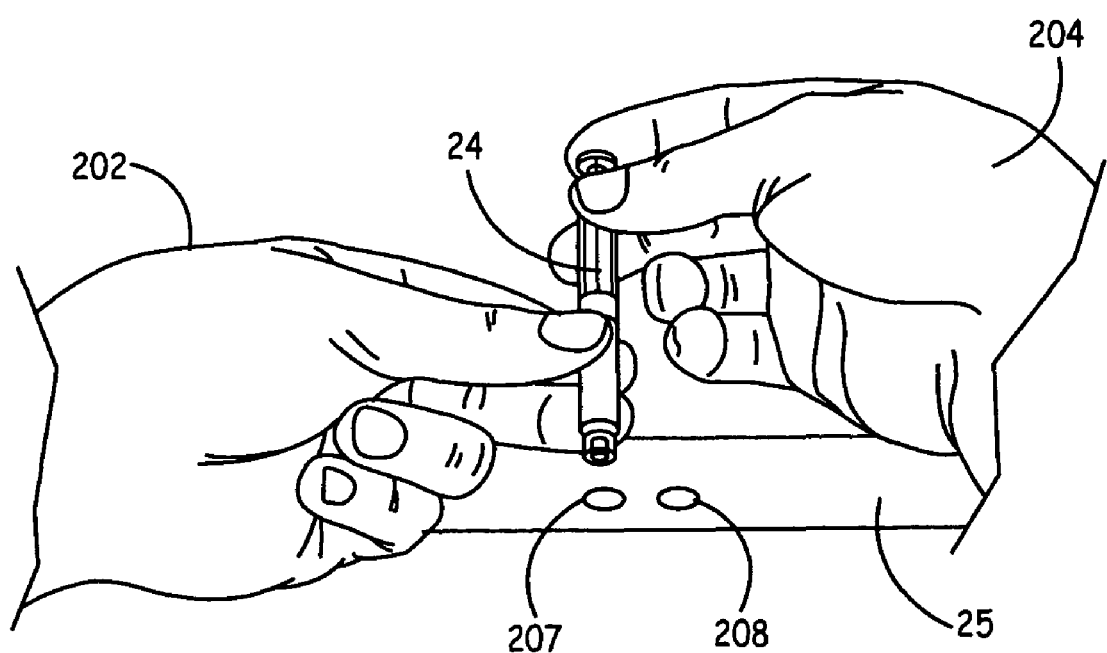
FIG. 3 depicts preparations for mixing an accelerant into a sealant on a sterile surface using the system of FIG. 1.

FIG. 2 depicts users hands 202, 204 mixing contents of syringes 24, 34 via mating union 206 to form mixture 207. The union 206 may be, for instance, a male and a female LUER LOK interconnection. FIG. 3 depicts a user dropping a volume of the mixture 207 from syringe 24 onto sterile surface 25. A drop of accelerant solution 208 has already been metered out onto sterile surface 25 from accelerator syringe 44. Syringe 26 and 44 are proportioned to make drops of comparable size, bearing in mind that differences in viscosity may require different orifice sizes.

Figure 4:
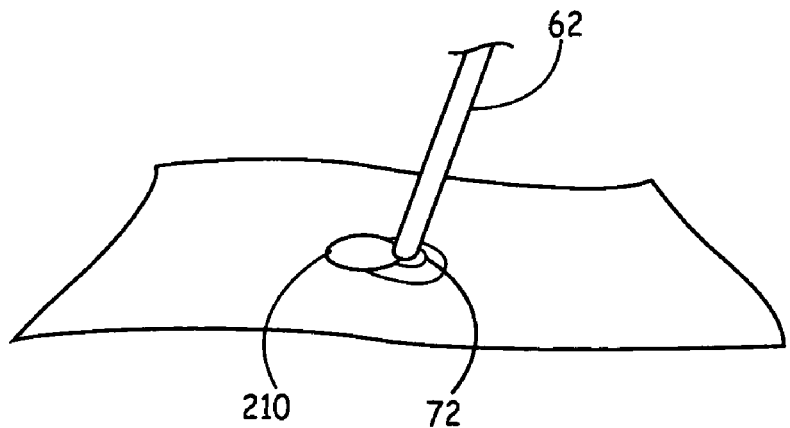
FIG. 4 depicts mixing components with the system of FIG. 1.

The user mixes mixture 207 and accelerant drop 208 together as in FIG. 4, using applicator stir rod end 72, forming mixture 210. User picks up a volume 220 (a drop) of mixture 210 as in FIGS. 5 and 6, using tip 68. Tip 68 is configured to provide a controllable amount of solution in a predetermined volume range so that the user can conveniently pick up as much solution as is reasonably needed; not too much and not too little.

For instance, the tip can be sized and proportioned to provide a drop in a range or subrange from about 10 microliters to about 500 microliters; artisans will immediately appreciate that all the ranges and values within the explicitly stated ranges are contemplated, e.g., from about 10 microliters to about 100 microliters, from about 20 microliters to about 200 microliters, less than about 100 microliters, or less than about 50 microliters. Such a range can be controlled by providing a taper, surface area, and hydrophobicity of the tip in light of a density of the solution; as in FIG. 6, the surface is relatively hydrophobic to cause the solution to bead and form a drop as opposed to spreading more broadly on the tip to provide a larger drop size. The surface area of the tip, and consequently the size of the tip, as well as its hydrophobicity control the size of the droplet that is naturally picked up. Some embodiments further control a size of droplet pickup by capillary forces created by including a feature on the applicator tip. Such feature may be, for example, a dimple, a crescent, a groove, a slit, a slot or other indentation. For the case wherein the applicator tip material is hydrophobic, when it contacts a hydrophilic tissue surface, e.g., an ophthalmic surface, it gives up the droplet and thus delivers it to the surface.

In general, for delicate tissues, e.g., a cornea, the applicator tip may be of a type that is atraumatic to the corneal or other delicate tissue surfaces, so as to not induce trauma, such as a corneal abrasion during normal application manipulation. A closed cell foam is well suited for the material of the applicator tip. Also suitable is a hydrophobic closed cell foam, such as a polyethylene foam. In general, the applicator tip does not absorb a significant quantity of liquid by itself, since this can create a variability in the amount of material delivered to the application site. Often the amount needed to be delivered is less than 10 microliters, which is smaller than one drop; for instance, ophthalmic sealant applications typically require small volumes of materials. If the applicator tip is made from a sponge or other material that absorb a significant amount of the liquid, then the application will have variability. Application of too much of a material, e.g., as in a hydrogel to the surface of the cornea, can create patient discomfort. Consequently selection of the tip material, size, surface characteristics, and bulk characteristics is important. Accordingly, applicator materials may be chosen that absorb less than about 30%, less than about 20%, less than about 10%, or essentially 0% of a solution's volume, including the case wherein the volume is less than: about 100, about 50, about 20, or about 10 microliters. As is apparent, embodiments of the applicator may have one or more of these features.

Figure 5:
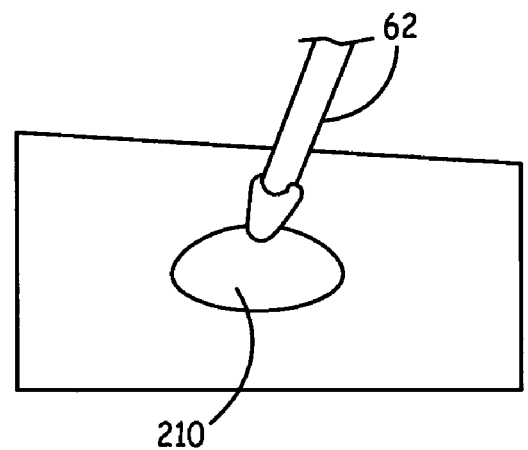
FIG. 5 depicts taking up a small volume of sealant using the system of FIG. 1.
Figure 6:
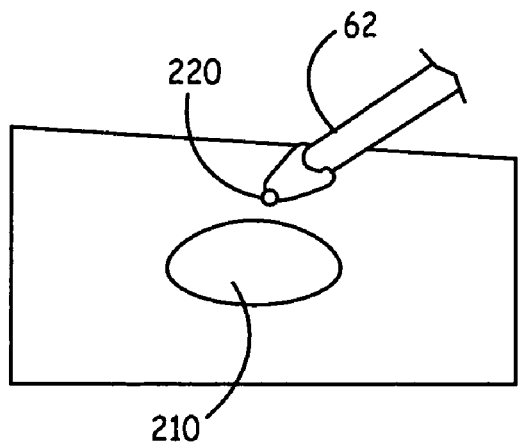
FIG. 6 depicts a small volume of sealant taken up with an applicator according to the system of FIG. 1.

As depicted in FIGS. 4-6, mixing is performed on a sterile surface. The system may include a sterile surface for the mixing process. The sterile surface may be substantially impermeable to water, meaning that essentially no water is lost into the surface material over about sixty minutes; thus small drops placed on the surface will not be dissipated thereby.

The sterile surface may be substantially hydrophobic meaning that a 100 microliter drop of distilled water placed on its surface will have a contact angle as measured by the static sessile drop method of more than about 75 degrees, with the contact angle being the angle between the material underlying the drop and the tangent of the drop's exterior at the material, as is customary in these arts. Similarly, the sterile surface may be hydrophobic meaning the contact angle is more than about 90 degrees, or highly hydrophobic meaning that the contact angle is more than about 120 degrees. The term at least substantially hydrophobic means a contact angle of more than about 75 degrees and includes highly hydrophobic surfaces. Contrariwise, substantially hydrophilic means a contact angle of less than about 75 degrees and highly hydrophilic means a contact angle of less than about 30 degrees. Adjusting the hydrophobicity of the sterile surface contributes to optimizing drop shapes for convenient access, aiding mixing by facilitating movement of drops from one location to another, and addressing unwanted movement or sliding of a drop. Hydrophilic materials cause an aqueous solution to spread on a surface, while hydrophobic materials tend to cause an aqueous solution to contract. Artisans reading this application will be able to choose materials or coatings to control the hydrophobicity of the surface.

The sterile surface is provided with the system in some embodiments. This surface can be part of packaging of the syringes or applicators. For instance a pouch that contains the whole system can have all or part of its surface useable as a sterile surface. This surface may be substantially flat. For instance, a pouch may be made that can be peeled apart into two or more portions that are fully detachable or partially detached to leave a point of union between them. For instance, two sheets of material may be bonded together at or near their edges, with unbonded margin or margins for grasping to peel the sheets apart. In some embodiments, a pouch comprises a foil/polymer laminate or a polymer film or laminate backing that is separable from a molded member, with the molded member receiving a component, e.g., a syringe or applicator.

The backing may serve as a top or bottom. In FIG. 1, the sterile surface is backing 25, which is fully detachable from its pouch. One class of backing is a laminate of polyethylene (inner side), aluminum foil, polyethylene and polyethylene terephthalate (PET) on the outside. The mixing is to be performed on the PET outer layer. PET is at least substantially hydrophobic, with its degree of hydrophobicity being controllable by its treatment. Other materials are available that are sterilizable and at least substantially hydrophobic, for instance certain engineering polymers.

By way of illustrating the invention, some embodiments of sealants that can be adapted to the systems described herein are described in U.S. Pat. No. 6,566,406 or U.S. Pat. No. 5,410,016, each of which are hereby incorporated by reference herein to the extent they do not contradict what is explicitly disclosed herein. These describe precursors that can be reacted to form a material, e.g., a hydrogel. The precursors are not reacted until they are combined in a favorable chemical environment, e.g., a suitable pH or by the presence of an initiator and/or catalyst for initiation or polymerization chain propagation. In some cases, the further addition of external energy is required, as in a light that triggers photopolymerization. In some cases only one precursor is needed to form a crosslinked hydrogel. In other cases two precursors with distinct functional groups that react with each other to form covalent bonds are needed. Other agents can be added, provided they do not interfere with the polymerization process or create materials with undesirable properties. Some precursors comprise polyethylene oxide, a term as used herein that includes polyethylene glycol (PEG).

Accordingly, by way of example, a first polymer precursor may be placed into a first syringe, either in solution or as a powder. A second precursor that reacts with the first precursor may be placed into a second syringe. The syringe contents are mixed together, e.g., as in FIG. 2. The accelerant may in a third syringe and provided as a buffer of adequate strength to change a pH of the mixture so that functional groups on the precursors quickly react with each other. Alternatively, an accelerant may be an initiator, e.g., a free radical initiator that decomposes to provide initiator radicals (a peroxide, for instance) or a photoinitiator. The term accelerant is a broad term that refers to initiators that are necessary to start a reaction and also to agents that cause the polymerization and gelation time of a precursor (or precursor mixture) to increase by at least a factor of about 5. A gelation time is the time required for a solution to change from a liquid to a gel by formation of polymers or crosslinking of materials. Polymerization is a broad term that refers to formation of a polymer by a monomer or macromer and includes chemical reactions of precursors that lead to formation of covalently crosslinked material by formation of covalent bonds between functional groups, e.g., electrophiles and nucleophiles. Physical crosslinking processes may be adapted to the system as well, with physical crosslinking referring to crosslinks formed by non-covalent bonding, e.g., charge-charge ionic bonding, or microdomain separation with hydrophobic association or crystallization.

One embodiment includes of components for preparation of a polyethylene glycol (PEG) bandage and a delivery system packaged in a single use kit. A PEG powder is placed in a syringe in a nitrogen filled foil pouch containing a 1.2 mL female LUER-LOK syringe with end-cap, e.g., a polyethylene glycol succinimidyl glutarate (PEG SG) powder, optionally with a dye or imaging agent (e.g., direct-visual, radiopaque). Also placed in the kit is diluent LUER-LOK syringe with end-cap containing a diluent solution, which may be an aqueous solution consisting of a precursor with amine and/or thiol functional groups. Also placed in the kit is a male LUER LOK syringe with end-cap containing accelerator solution such as an aqueous buffer solution with a concentration effective to increase a pH of an equal volume of a mixture of the other syringes to at least about 8 or at least about 9 pH. Also placed in the kit is a glassine pouch containing two atraumatic foam-tipped applicators having, for instance a polycarbonate stir-handle and a polyethylene foam tip. In use, the PEG powder in the appropriate syringe is reconstituted with the diluent syringe contents. A single drop of the PEG is mixed with a single drop of the accelerator solution, on the surface of the provided sterile surface, which can be an interior foil pouch portion. An applicator stir-handle is then used to mix the two drops and to apply on to the target tissue. The mixed liquid can be prepared to have a working time of 15 to 40 seconds prior to gelation, or from about 30 seconds to about 300 seconds' artisans will immediately appreciate that all the ranges and values within the explicitly stated ranges are contemplated. Depending on the composition of sealant, a user can survey the tissue to determine that there is an absence of active leaking at site during application. Indeed, some incisions on an eye may require stromal hydration prior to application to ensure the site is dry and an active leak is not present. A dye may be included, e.g., to provide a blue color to marks the area where the material has been applied. Sealant compositions are further disclosed in U.S. Pat. No. 7,211,651, which is hereby incorporated by reference to the extent it does not contradict what is explicitly disclosed herein.

Syringes may be used to mix and dispense materials dropwise. Alternatives include bulbous droppers and pipettes or pipetting systems, e.g., as in U.S. Pat. Nos. 703,101, 3,158, 183, 4,117,728, or 5,154,702, each of which are hereby incorporated by reference to the extent they do not contradict what is explicitly disclosed herein. The term dropper, as used herein, refers to such devices. The term bulbous dropper refers to a dropper that relies on a manually squeezed bulb to force out a fluid. In general, users can manually perform dropwise dispensing with good accuracy using a suitable dropper. Single-use droppers are generally convenient for purposes of sterility.

Some embodiments are adapted for use in an ophthalmic applications, e.g., as in U.S. Ser. No. 11/825,848, which is hereby incorporated by reference to the extent it does not contradict what is explicitly disclosed herein. In this aspect, the use of small volumes is typical and the advantages of these systems for addressing the needs of small-volume users are substantial. For instance lacerations and/or surgical incisions on the eye, e.g., cornea, can be sealed using these systems.

Some embodiments relate to a method for making a combination of medical sealant components in a packaging comprising providing, in a single housing: a first medical sealant component in a first dropper, an aqueous solution in a second dropper, a second medical sealant component disposed in either the first dropper or the second dropper, an aqueous solution of an accelerant in a third dropper that accelerates gelation of a mixture of the first sealant component and the second sealant component to form a hydrogel sealant, a soft-tipped applicator, and a water-impermeable sterile surface removable from the housing. The housing may be, for instance, a box, pouch, plastic container, or some combination thereof. In general, the housing is designed for, and made of materials for, sterilization by conventional medical methods, e.g., radiation or ethylene oxide. Such a system may have a sterile pouch that contains at least one member of the group consisting of the first dropper, the second dropper, the third dropper and the soft-tipped applicator, with the sterile surface (which may be water-impermeable) being part of the pouch, e.g., an interior surface of the pouch. In some embodiments, the user peels the pouch open, with the pouch consisting essentially of two subcomponents designed to be peeled away, or with a tab graspable to open the pouch. The sterile surface may be separable from the pouch to form a substantially flat surface. One or more of the droppers may be a syringe and adapted to mate with each other to provide for syringe-to-syringe mixing, with one or more of the syringes optionally configured not to mate with the others, e.g., in the case of an accelerant not intended to mix with contents of the other syringes until immediately prior to use. Such a dropper, e.g., syringe, may comprise a dispensing orifice sized to dispense a drop of aqueous solution in a volume of between about 50 to about 100 microliters. The housing may include a soft-tipped applicator, e.g., with a round-pointed sponge that provides the soft tip. The sterile surface may be hydrophobic or substantially hydrophobic. In the case of mixing organic solutions, the sterile surface may comprise a mixing portion that is impervious to dissolution or attack by the solvent, bearing in mind that many conventional materials dissolve, become tacky, or release chemicals into organic solvents. Similarly, droppers may be configured to one impervious to organic solvents. Embodiments include the components of such methods, e.g., as in a combination of medical sealant components in a packaging comprising a single housing that contains: a first medical sealant component in a first dropper, an aqueous solution in a second dropper, a second medical sealant component disposed in either the first dropper or the second dropper, an aqueous solution of an accelerant in a third dropper that accelerates gelation of a mixture of the first sealant component and the second sealant component to form a hydrogel sealant, a soft-tipped applicator, and a water-impermeable sterile surface removable from the housing.

It is claimed:

1. A method for making a combination of a medical sealant components in a packaging comprising providing, in a single housing:
    a first medical sealant component in a first dropper,
    an aqueous solution in a second dropper,
    a second medical sealant component disposed in either the first dropper or the second dropper,
    an aqueous solution of an accelerant in a third dropper that accelerates gelation of a mixture of the first sealant component and the second sealant component to form a hydrogel sealant, wherein the gelation is achieved as a product of a reaction between the first component and the second component, and the accelerant accelerates the reaction,
    a soft-tipped applicator, and
    a water-impermeable sterile surface removable from the housing.

2. The method of claim 1 further comprising a sterile pouch that contains at least one member of the group consisting of the first dropper, the second dropper, the third dropper and the soft-tipped applicator, with the water-impermeable sterile surface being an interior surface of the pouch.

3. The method of claim 2 wherein the sterile surface is separable from the pouch to form a substantially flat surface.

4. The method of claim 3 wherein the sterile surface is separable by manual peeling by a user.

5. The method of claim 2 wherein the sterile surface further comprises a tab for a user to grasp to peel the sterile surface from the pouch.

6. The method of claim 1 wherein the first dropper is a first syringe and the second dropper is a second syringe, with the first syringe and second syringe adapted to mate with each other to provide for syringe-to-syringe mixing.

7. The method of claim 6 wherein the third dropper is a third syringe that does not mate with the first syringe or the second syringe.

8. The method of claim 7 wherein the second and third syringe comprises a dispensing orifice sized to dispense a drop of aqueous solution in a volume of between about 20 to about 100 microliters.

9. The method of claim 1 wherein the soft-tipped applicator comprises a round-pointed sponge that provides the soft tip.

10. The method of claim 1 wherein the sterile surface is at least substantially hydrophobic.

11. A combination of medical sealant components in a packaging comprising a single housing that contains:
a first medical sealant component in a first dropper,
an aqueous solution in a second dropper,
a second medical sealant component disposed in either the first dropper or the second dropper,
an aqueous solution of an accelerant in a third dropper that accelerates gelation of a mixture of the first sealant component and the second sealant component to form a hydrogel sealant,
a soft-tipped applicator, and
a water-impermeable sterile surface removable from the housing.

12. The combination of claim 11 further comprising a sterile pouch that contains at least one member of the group consisting of the first dropper, the second dropper, the third dropper and the soft-tipped applicator, with the water-impermeable sterile surface being an interior surface of the pouch.

13. The combination of claim 12 wherein the sterile surface is separable from the pouch to form a substantially flat surface.

14. The combination of claim 13 wherein the sterile surface is separable by manual peeling by a user.

15. The combination of claim 12 wherein the first dropper and the second dropper mate with each other to provide for dropper-to-dropper mixing.

16. The combination of claim 15 wherein the third dropper is disabled for mating with the first dropper and the second dropper.

17. The combination of claim 16 wherein the third dropper comprises a dispensing orifice sized to dispense a drop of aqueous solution in a volume of between about 50 to about 100 microliters.

18. The combination of claim 12 wherein the pouch comprises sterile foil laminate or sterile polymer that is at least substantially hydrophobic and provides the sterile surface.

19. The combination of claim 11 wherein the soft-tipped applicator comprises a brush that provides the soft tip.

20. The method of claim 8 wherein the third syringe and the second syringe are proportioned to make drops of substantially equal sizes.

21. The combination of claim 17 wherein the third dropper and the second dropper are proportioned to make drops of substantially equal sizes.

22. The method of claim 9 wherein the soft tip is configured to provide a controllable amount of solution in a predetermined volume range of less than 100 microliters.

23. The combination of claim 11 wherein the soft tip is configured to provide a controllable amount of solution in a predetermined volume range of less than 100 microliters.

* * * * *